United States Patent [19]

Lukas et al.

[11] 4,423,043

[45] Dec. 27, 1983

[54] AQUEOUS LIQUID FORMULATIONS FOR CONTROL OF BACTERIAL AND PROTOZOAL DISEASES

[75] Inventors: Gerhard Lukas, Muttenz; Kaya Atasoy, Münchenstein, both of Switzerland

[73] Assignee: Ciba-Geigy Corporation, Ardsley, N.Y.

[21] Appl. No.: 345,990

[22] Filed: Feb. 5, 1982

Related U.S. Application Data

[63] Continuation-in-part of Ser. No. 216,587, Dec. 15, 1980, abandoned, which is a continuation of Ser. No. 59,425, Jul. 20, 1979, abandoned.

[30] Foreign Application Priority Data

Aug. 1, 1978 [CH] Switzerland ............... 8216/78

[51] Int. Cl.³ .................................. A61K 31/625
[52] U.S. Cl. ............................................ 424/229
[58] Field of Search ............................. 424/229

[56] References Cited

U.S. PATENT DOCUMENTS

| 4,031,214 | 6/1977 | Easterbrook | 424/229 |
| 4,133,879 | 1/1979 | Casals | 424/229 |
| 4,332,796 | 6/1982 | Los | 424/229 |
| 4,374,826 | 2/1983 | Armstrong | 424/229 |

FOREIGN PATENT DOCUMENTS

| 2311214 | 9/1973 | Fed. Rep. of Germany . | |
| 2400218 | 7/1974 | Fed. Rep. of Germany . | |
| 2445401 | 3/1975 | Fed. Rep. of Germany . | |
| 2631779 | 1/1978 | Fed. Rep. of Germany | 424/80 |
| 2631780 | 1/1978 | Fed. Rep. of Germany | 424/80 |
| 832877 | 7/1960 | France | 424/229 |
| 1176395 | 1/1970 | United Kingdom . | |

OTHER PUBLICATIONS

Fiedler, "Lexikon der Hilfstoffe für Pharmazie, Kosmetik, und . . . ", pp. 158, 159, 580 excerpts (1971).
Magyar Allatorvorsok Lapja 12 (1975) 833-836.

Primary Examiner—Ethel G. Love
Attorney, Agent, or Firm—Frederick H. Rabin; Bruce M. Collins

[57] ABSTRACT

A stable aqueous formulation containing as active substance an active-substance combination consisting of 2,6-diamino-5-(3',4', 5'-trimethoxybenzyl)-pyrimidine (trimethoprim) and either sulfachloropyrazine of the formula

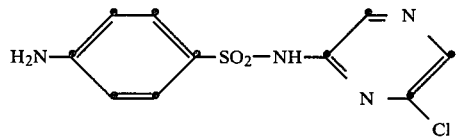

or a salt thereof,
or sulfachloropyridazine of the formula

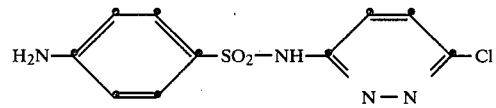

or a salt thereof, for combating bacterial and protozoal diseases in animals by means of drinking water application. Besides the stated active substances, the formulation contains an organic solvent, a solubilizer, a surfactant and water.

1 Claim, No Drawings

AQUEOUS LIQUID FORMULATIONS FOR CONTROL OF BACTERIAL AND PROTOZOAL DISEASES

CROSS REFERENCE TO RELATED APPLICATIONS

This is a continuation-in-part of Application Ser. No. 216,587, filed on Dec. 15, 1980, which in turn is a continuation of Application Ser. No. 059,425, filed on July 20, 1979, both now abandoned.

The present invention relates to a stable aqueous formulation for combating bacterial and protozoal diseases, which formulation is based on an active-substance combination consisting of (a) either N-[6-chloropyridazinyl-(3)]-sulfanilamide (=sulfachloropyridazine) or N-[6-chloropyrazinyl-(2)]-sulfanilamide (=sulfachloropyrazine) and (b) 2,6-diamino-5-(3′,4′,5′-trimethoxybenzyl)-pyrimidine (=trimethoprim). Besides the stated active substances and water, the formulation contains an organic solvent, a solubilizer and a surfactant component in specific quantitative proportions.

The effectiveness of sulfonamide-trimethoprim compositions in the control of infectious diseases in humans and in animals is well known. The particular importance of the trimethoprim component derives from the potentiation of the antibacterial and antiprotozoal activity of the sulfonamides.

The administration of customary active-substance combinations to animals presents however certain difficulties. Thus, in the case of administration in the solid form, by addition to the fodder, a treatment with any promise of success is in the majority of cases not possible since sick animals in general greatly reduce the intake of feed, or may even refuse it completely. On the other hand, there is usually no reduction in the quantity of water consumed by the animals, so that medication of the animals' drinking water offers a possibility of the enteral introduction of active substances into the animal organism.

A further possibility is the parenteral administration of the active substances by means of injection; however, in view of the need for prophylactic application to numerically extensive groups of animals, which are a major factor in modern livestock production, the injection method is not practicable for reasons of cost. Here, too, medication of the drinking water constitutes a useful logical alternative. It is shown therefore that the provision of a stable drinking water solution of sulfachloropyr(id)azine-trimethoprim combinations adapted to meet practical requirements is of great importance for the control of infectious diseases in animals. Furthermore, the medication of drinking water for some species of productive livestock, for example poultry, is in practice the only possibility of applying treatment to large groups of animals.

Since neither trimethoprim nor sulfachloropyridazine or sulfachloropyrazine have sufficient solubility in water, there are generally used the water-soluble salts of these compounds. The problem arising here however is that on combination of the formed salt solutions with fairly large amounts of water, bringing the pH-value near to the neutral point, a precipitation of the active substances occurs.

The preparation of therapeutically suitable drinking-water solutions creates therefore considerable difficulties, major factors in this respect being lacking stability of the undiluted commercial concentrates, preservation of the active-substance concentration in the diluted application form and avoidance of precipitation. This applies all the more at the present time because of the introduction in practice, to an ever increasing extent, of automatic drinking devices. The feeding in of medicaments occurs in the case of apparatus of this type in most cases continuously by means of dosing devices which operate according to the principle of proportional dispensation. The desired concentration of medicament in the drinking water (final dilution) in determined (a) by the ratio of the aperture cross-section of the water supply pipe to that of the medicament-solution supply pipe, and (b) by the concentration of this medicament-solution (intermediate dilution), which has to be adjusted in the individual case to the flow parameters of the apparatus concerned. The smooth functioning of devices of this kind depends however on, amongst other things, the fully satisfactory condition of the solutions to be dispensed. The precipitation of solid deposits in the solutions provided for preparing the final dilution, or that occurring during dilution and administration, will inevitably lead to variations in the dosage, in consequence of which a reliably controlled treatment is no longer ensured. The presence of solid constituents in the intermediate dilutions of the drinking-water solutions containing the active substances can moreover result in a disturbance of the functioning of the dispensing apparatus, and this in turn gives rise to losses of valuable material and to additional labour costs.

In order to overcome these difficulties, it has already been suggested in the case of sulfonamides of different chemical structure in admixture with trimethoprim that active-substance combinations be converted into a form suitable for therapeutic purposes by the use of organic solvents or solubility promoting agents.

The German Offenlegungsschrift No. 2,311,214 mentions, in addition to the formation of solid combinations of trimethoprim and N-(4,5-dimethyl-3-isooxazolyl)-sulfanilamide as feed additives, the preparation of an injection solution having a low water content and a total active-substance content of about 25%. There are also mentioned aqueous formulations wherein the content of the stated active-substance combination for oral administration can be lowered to 5% and below by dilution with water. There is however nothing to be derived from the information contained in the said publication which gives any indication of a general possibility of producing stable sulfonamide/trimethoprim combinations which can be diluted with drinking water and which remain stable over several days also in the diluted state.

The British Patent Specification No. 1,176,395 mentions injectable formulations of trimethoprim with a series of sulfonamides, such as 5,6-dimethoxy-4-sulfanilamidopyrimidine, 4,6-dimethyl-2-sulfanilamidopyrimidine, 2,4-dimethoxy-6-sulfanilamidopyrimidine or 3,4-dimethyl-5-sulfonamidoisoxazole, with active-substance concentrations of 12–14%. In order to produce these formulations, the active-substance components have to be taken separately from one another into solution, the sulfonamide being dissolved either together with bases or in one case as Na salt in water, and the trimethoprim in organic solvents or solubilizers and the solutions are then mixed together.

On the other hand, for the production of the liquid formulations of trimethoprim with sulfamethazole or sulfacetamide, there is described in the German Offenlegungsschrift No. 2,400,218 a different procedure. The trimethoprim is firstly dissolved, with the addition of acid, in water, and the sulfonamide is then added together with organic solvents or solubilizers. The active-substance combinations produced in this manner are suggested, according to the above-mentioned patent specification, for injection or for oral administration. There is given as active-substance content in the case of the sulfonamide a proportion of 1 to 40%, and in the case of the sulfonamide potentiating agent, trimethoprim, of 1 to 10%.

It can be seen already from this range of dissolving suggestions that only by means of specific formulations not hitherto known can the problems arising in connection with specific active-substance combinations be overcome, for because of the considerable structural differences between the various types of sulfonamides a prediction of the properties to be expected is not possible.

The patent specifications of the prior art relate therefore in particular to sulfonamide-trimethoprim formulations of fairly high concentration with and without the addition of water, which are primarily intended for administration by injection, but which are sometimes recommended also for drinking water application. In most cases, the dilution with water is essential for this purpose in order to adjust the active-substance concentration to give the lower concentration required for this application, and in the concentration range of the intermediate dilutions necessary for automatic drinking devices there occur more or less rapidly precipitations, an effect which results in these solutions becoming unusable. In the case of the formulations already suggested for application in drinking water, there is the disadvantage that the intermediate dilutions remain clear, with a constant level of concentration, for only a very short time and thus cannot be stored. This factor renders therefore necessary, depending on the frequency of application, the frequent preparation of fresh active-substance solutions in water, which are intended for rapid consumption, whilst the deteriorated solutions have to be discarded.

Taking as a basis the already mentioned advantages offered by the administration of sulfachloropyr(id-)azinetrimethoprim combinations for prophylactic and therapeutic treatment by means of drinking water application compared with administration in the form of additives to dry fodder or injections, there is clearly an urgent need to provide aqueous solutions of the stated active-substance combinations which, with regard to clarity and solubility are stable (a) within a broad concentration range and (b) over a considerably period of time.

A testing of the aqueous formulations proposed in the German Offenlegungsschrift No. 2,311,214 and in the British Patent Specification No. 1,176,395 showed however that these formulations were not satisfactory with respect to their carrier and distributing substances when applied to the active-substance combinations of the present invention, so that it was not possible in practice to produce with these active substances useable stable and clear aqueous solutions.

There is furthermore an additional problem: reference is made in publications to the fact that some of the solvents and solubility-promoting agents suggested in the aforementioned patent specifications and Offenlegungsschriften as functional auxiliaries, for example N,N-dimethylacetamide, propylene glycol, dimethylformamide, glycerin formal and polyethylene glycols, cannot be considered safe from a pharmacological-toxic standpoint (cp. in this respect German Offenlegungsschrift No. 2,631,779; H. P. Fiedler, Lexikon der Hilfsstoffe für Pharmazie, Kosmetik, 1971; and Prax. Pneumolog. 28 (19 (1971) 491).

The problems described in the foregoing have been overcome by the present invention in the following manner: The liquid formulations according to the invention, which are dilutable with water, have the following composition:

2,6-diamino-5-(3',4',5'-trimethoxybenzyl)-pyrimidine (trimethoprim) and either sulfachloropyrazine of the formula Ia

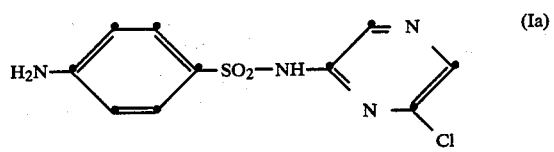

or a salt thereof,
or sulfachloropyridazine of the formula Ib

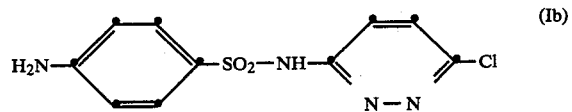

or a salt thereof,
in the quantity ratio of 1:1 to 1:20, preferably 1:4 to 1:5, with a total proportion of 15 to 25 percent by weight being dissolved in a physiologically compatible, water-miscible solvent, a solubilizer,
a surfactant and water, and a base in the case where the sulfonamide is not used as a salt, in which composition the solvent used, besides water, is N-methylpyrrolidone, on its own or in combination with glycol monoethyl ether; the surfactant used is bis-(2-ethylhexyl)-Na-sulfosuccinate;
and the solubilizer used is one selected from the group comprising hydroxyethyltheophylline, nicotinic acid amide and sodium benzoate; and the base used is ethanolamine. With regard to the amounts used, they are preferably 60-80 percent by weight of solvent, 0.1-1.0 percent by weight of surfactant, and 1-10 percent by weight of solubility-promoting agent. In the case of the solubilizer used, the following amounts are to be considered particularly preferred: for hydroxyethyltheophylline or sodium benzoate 1-10 percent by weight, and for nicotinic acid amide 2-4 percent by weight.

The present formulations according to the invention render it possible to produce not only concentrated aqueous solutions which remain clear over a prolonged period of time and under normal conditions are unaffected by storage, but, surprisingly, also solutions dilutable with water which retain their stability throughout a wide dilution range over an application period of several days. Thus, on the one hand the concentrated forms are stable to the effects of storage and transport, whilst on the other hand the diluted solutions at the place of application can be stored in a stable form as intermediate dilutions over a period of several days as occasion demands, when they can then be converted, without any particular effort, into the desired final, still stable, dilution form to meet the therapeutic requirements. The simple dosing and application method which is thus rendered possible, and which can be performed without loss of valuable active substances, serves in particular to improve the therapeutic efficiency by virtue of more precise dosing of active substance, and also to produce the expenditure on material and labour.

The advantageous dilution scheme based on the formulations according to the invention is characterised by the following factors: The total amount of active substance in the formulations is in general 15–25 percent by weight. From these formulations are prepared, in amounts depending on application requirements, clear intermediate dilutions, in which, by the addition of drinking water in the ratio of 5:1 to 50:1, the concentration of active substance can be appropriately reduced without the stability of the intermediate dilutions suffering as a result. These intermediate dilutions of active substance, which remain stable over a period of several days, are stored in the dispensing devices (dispensers) at the place of application, under normal temperature conditions. The amounts of active-substance solution which are required for the treatment of the animals are then automatically taken from these dispensers, and by means of suitable dosing devices the final respective concentration required for the treatment is accurately adjusted by the addition of drinking water. In the case of this final dilution, the proportion of active substance is in general below 1 percent by weight, in some cases even below 0.1 percent by weight down to 0.001 percent by weight. The stability of the formulations according to the invention, which properly is retained even after high dilutions with water, render possible, by application of the dilution principle described, an exact determination of the active-substance dose being administered, so that consequently accurate checking and regulation of the specific treatment are provided.

In the technical world there have so far become known no objections on toxicological grounds to the functional auxiliaries, such as solvents and solubility-promoting agents, used for the production of the formulations according to the invention.

The active-substance combinations contained in the formulations according to the invention have a broad antibacterial and antiprotozoal spectrum of activity, inter alia against in particular: Escherichia coli, Coccidia, Salmonellae, Staphylococci and Streptococci, and are therefore especially suitable for the prophylactic and therapeutic treatment of infectious diseases in domestic and productive animals, such as poultry, pigs, calves, cattle, sheep and goats. The formulations according to the invention assume therefore, by virtue of the creation of excellent solubility properties, great importance as active-substance carriers for the medication of drinking water precisely for the treatment of large groups of animals, which are at the present time customary in agricultural intensive production.

The active substances used in the formulations according to the invention are known. Thus, 2,6-diamino-5-(3',4',5'-trimethoxybenzyl)-pyrimidine (trimethoprim) is described in Brit. Pharmakopoeia 1973, 484, and N-[6-chloropyridazinyl-(3)]-sulfanilamide (sulfachloropyridazine) in the Handbook of Veterinary Drugs, Ed. Springer N.Y. 1974, 564, as well as in Ullmanns Enzyklopädie d. Techn. Chemie, Publisher: Chemie Weinheim, 3rd Edition, Vol. 15, and N-[6-chloropyrazinyl-(2)]-sulfanilamide (sulfachloropyrazine) is described in the Handbook of Veterinary Drugs, Ed. Springs N.Y. 1974, 564.

With respect to an active-substance combination consisting of sulfachloropyridazine and trimethoprim, which is mentioned in a general manner [cp. Magyar Allatorvosok Lapja 12, pp. 833–836 (1975)], there has hitherto been made in the literature no suggestion for overcoming the stated problems.

Active-substance combinations consisting of sulfachloropyrazine and trimethoprim have not been suggested hitherto.

The solvents, solubility-promoting agents and surfactants used as functional auxiliaries are known as such to those skilled in the art.

The active-substance formulations according to the invention are produced by the following process: the active substances, in the presence of a solubilizer and a surfactant, are dissolved, in a suitable vessel which can be darkened, with the maximum possible exclusion of light and with continuous stirring, in the major part of the intended solvent and water at 10° to 70° C., preferably at 10° to 50° C., the remainder of the solvent is subsequently added, and the solution is filtered, if necessary with the aid of filtering auxiliaries, for example kieselguhr. In order to accelerate filtration, the temperature can be raised slightly above that maintained during the dissolving process. It is also possible to additionally add to the formulations according to the invention preservatives, for example sorbic acid.

The following Examples, which illustrate the active-substance formulations according to the invention, were carried out at room temperature, with room temperature being understood, according to Ph. Eur. Vol. 1, as being the temperature range of 15° to 25° C.

EXAMPLE 1

15.48 g of sulfachloropyridazine, 3.33 g of trimethoprim, 3.0 g of hydroxyethyltheophylline and 0.5 g of sodium dioctylsulfosuccinate are dissolved in 8.0 g of demineralised water and about 70 g of N-methylpyrrolidone and 4.0 g of ethanolamine in a suitable vessel which can be darkened, with frequent shaking; the solution is then made up with about a further 6 g of N-methylpyrrolidone to 100 ml, and subsequently filtered, if necessary with the addition of a filtering auxiliary.

EXAMPLE 2

In a suitable vessel which can be darkened, 16.67 g of sulfachloropyridazine sodium, 3.33 g of trimethoprim, 3.0 g of nicotinic acid amide and 0.5 g of sodium dioctylsulfosuccinate are dissolved, with repeated shaking, in 20.0 g of water and about 60 g of N-methylpyrrolidone; the solution is then made up with about a further 8 g of N-methylpyrrolidone to 100 ml, and subsequently filtered, if necessary with the use of a filtering auxiliary.

EXAMPLE 3

In a suitable vessel that can be darkened, 14.72 g of sulfachloropyrazine, 3.33 g of trimethoprim, 5.0 g of hydroxyethyltheophylline and 0.5 g of sodium dioctylsulfosuccinate are dissolved, with repeated shaking, in 9.0 g of water and about 70 g of N-methylpyrrolidone and 4.0 g of ethanolamine; the solution is then made up with about a further 5 g of N-methylpyrrolidone to 100 ml, and is subsequently filtered, if necessary using a filtering auxiliary.

EXAMPLE 4

In a suitable vessel that can be darkened, 15.48 g of sulfachloropyridazine, 3.33 g of trimethoprim, 3.0 g of hydroxyethyltheophylline, 0.5 g of sodium dioctylsulfosuccinate and 0.2 g of sorbic acid are dissolved, with repeated shaking, in 8.0 g of demineralised water, 4.0 g of ethanolamine and about 60 g of N-methylpyrrolidone; the solution is then made up to 100 ml with N-methylpyrrolidone, and subsequently filtered, using is necessary a filtering auxiliary.

EXAMPLE 5

In a suitable vessel that can be darkened, 16.67 g of sulfachloropyridazine sodium, 3.33 g of trimethoprim, 3.0 g of sodium benzoate and 0.5 g of sodium dioctylsulfosuccinate are dissolved, with repeated shaking, in 20.0 g of demineralised water and about 60 g of N-methylpyrrolidone; the solution is made up to 100 ml with N-methylpyrrolidone, and subsequently filtered, using if necessary a filtering auxiliary.

EXAMPLE 6

In a suitable vessel that can be darkened, 16.67 g of sulfachloropyrazine sodium monohydrate, 3.33 g of trimethoprim, 3.0 g of hydroxyethyltheophylline and 0.5 g of sodium dioctylsulfosuccinate are dissolved, with repeated shaking, in 8.0 g of water, 19.26 g of glycol monoethyl ether and about 50 g of N-methylpyrrolidone; the solution is then made up to 100 ml with about a further 7 g of N-methylpyrrolidone, and subsequently filtered, using if necessary a filtering auxiliary.

In order to demonstrate the stability properties of the active-substance combinations according to the invention when they have been diluted with drinking water, a storage test was carried out on sulfonamide/trimethoprim combinations which had been formulated according to the Examples described in the foregoing. A comparison was made at the same time with a known sulfonamide/trimethoprim combination described in the USA Patent Specification No. 4,133,379.

EXAMPLE 7

Comparative test of long term stability of some sulfonamide/trimethoprim combinations after they have been diluted with drinking water 1. Active-substance combinations (formulations)
formulation A, produced according to Example 1 in the foregoing,
formulation B, produced according to Example 3 in the foregoing,
formulation C, produced according to Example 2 of the USA Patent Specification No. 4,133,879.

Procedure for carrying out the comparative test

The test formulations were diluted individually with drinking water in the ratio of 1:10 to 1:50.

The dilutions were stored in cylindrical glass vessels sealed against water vapour and each having a volume of 100 ml for 4 to 8 days at room temperature in a dark room. The specimens were examined during storage, at regular intervals of time, firstly with the naked eye and then microscopically.

The observed results are summarised in the following Table.

3. Results

| Dilution ratio | Total concentration of a.i. in % [1] | Condition of solution | Time [2] |
|---|---|---|---|
| Formulation A | | | |
| 1:20 | 0.94 | clear, without sedimentation | 4 days |
| 1:30 | 0.63 | clear, without sedimentation | 4 days |
| 1:40 | 0.47 | clear, without sedimentation | 4 days |
| 1:50 | 0.38 | clear, without sedimentation | 4 days |
| Formulation B | | | |
| 1:20 | 0.90 | clear, without sedimentation | 8 days |
| 1:30 | 0.60 | clear, without sedimentation | 8 days |
| 1:40 | 0.45 | clear, without sedimentation | 8 days |
| 1:50 | 0.36 | clear, without sedimentation | 8 days |
| Formulation C | | | |
| 1:10 | 2.4 | intense white cloudiness with subsequent sedimentation: no change up to end of test | several minutes |
| 1:30 | 0.8 | crystalline sedimentation, no change up to end of test | 3 hours |
| 1:40 | 0.6 | crystalline sedimentation, no change up to end of test | 3 hours |

[1] a.i.: sulfonamide + trimethoprim
[2] time until occurrence of changes in the clear state of the solutions

Observations

The tested formulations A and B (Examples 1 and 3 of the present invention) remain, in the form they are in after being diluted with drinking water, as clear stable solutions within a wide concentration range over a period of 4 or 8 days. There commences firstly after this length of time a slight clouding, which however does not result even over the following 2 days in sedimentation. This signifies for practical purposes a high degree of stability and a long duration of usability. The formulations of the present invention thus have the properties required, in mass livestock production, for the oral administration, by means of automatic dispensing devices, of sulfonamide/trimethoprim combinations diluted with drinking water.

The formulation C known from the prior art is on the other hand unsuitable by virtue of the fact that the precipitation of solid sediments in diluted solutions of formulation C occurs immediately or within a few hours. Over a period of 8 days, these sediments do not dissolve in the standing solution, nor do they dissolve as a result of slight stirring. On the contrary, there is observed on specimens under the microscope a trebling of the size of initially formed crystals and an increase in the total amount of crystals.

What is claimed is:

1. A concentrated but stable sulfonamide/trimethoprim formulation dilutable in livestock drinking water without causing sedimentation, which formulation comprises a solution of
(1) from 15 to 25%, by weight of the formulation, of a 1:4 to 1:5 by weight mixture of 2,6-diamino-5-

(3,4,5-trimethoxybenzyl)-pyrimidine and a sulfonamide selected from the group consisting of
(i) sulfachlorpyrazine,
(ii) a salt of sulfachlorpyrazine,
(iii) sulfachlorpyridazine, and
(iv) a salt of sulfachlorpyridazine;
(2) from 0.1 to 1.0%, by weight of the formulation, of sodium dioctylsulfosuccinate;
(3) from about 1 to about 10%, by weight of the formulation, of a solubilizer selected from the group consisting of hydroxyethyltheophylline, nicotinic acid amide and sodium benzoate;
(4) from about 60 to 80%, by weight of the formulation, of a liquid carrier, said liquid carrier consisting essentially of
(i) an organic solvent selected from the group consisting of (a) N-methylpyrrolidone and (b) a combination of N-methylpyrrolidone and glycol monoethyl ether, and
(ii) water; and
(5) when a salt of sulfachlorpyrazine or a salt of sulfachlorpyridazine is present, a quantity of ethanolamine sufficient to solubilize said salt.

* * * * *